(12) United States Patent
De Heinrich et al.

(10) Patent No.: US 9,956,161 B2
(45) Date of Patent: May 1, 2018

(54) COSMETIC PREPARATIONS

(75) Inventors: Stephen De Heinrich, London (GB); Colette Margeurite Louise Haydon, London (GB)

(73) Assignee: Omorovicza Cosmetics Limited, London (GB)

(*) Notice: Subject to any disclaimer, the term of this patent is extended or adjusted under 35 U.S.C. 154(b) by 0 days. days.

(21) Appl. No.: 13/499,753

(22) PCT Filed: Sep. 30, 2010

(86) PCT No.: PCT/GB2010/051633
§ 371 (c)(1),
(2), (4) Date: Jun. 25, 2012

(87) PCT Pub. No.: WO2011/039541
PCT Pub. Date: Apr. 7, 2011

(65) Prior Publication Data
US 2012/0258152 A1 Oct. 11, 2012

(30) Foreign Application Priority Data
Oct. 2, 2009 (GB) .................... 0917254.5

(51) Int. Cl.
*A61K 8/99* (2017.01)
*A61Q 19/00* (2006.01)
*A61K 8/14* (2006.01)
*A61K 8/96* (2006.01)

(52) U.S. Cl.
CPC ............... *A61K 8/965* (2013.01); *A61K 8/99* (2013.01); *A61Q 19/00* (2013.01)

(58) Field of Classification Search
None
See application file for complete search history.

(56) References Cited

U.S. PATENT DOCUMENTS

| 5,106,624 A * | 4/1992 | Bertini ...................... 424/401 |
| 5,376,379 A | 12/1994 | Fabre et al. |
| 5,711,965 A * | 1/1998 | Ghyczy et al. ............... 424/450 |
| 2006/0134156 A1* | 6/2006 | Marion .......................... 424/401 |
| 2009/0022819 A1* | 1/2009 | Gueniche et al. ............ 424/717 |
| 2009/0028826 A1* | 1/2009 | Breton et al. ............... 424/93.4 |
| 2009/0060962 A1* | 3/2009 | Castiel et al. ................ 424/401 |

FOREIGN PATENT DOCUMENTS

| EP | 0504043 A1 | 9/1992 |
| EP | 0699432 | 3/1996 |
| EP | 1166764 A1 | 1/2002 |
| WO | 9206666 | 4/1992 |
| WO | 9513793 | 5/1995 |

OTHER PUBLICATIONS

"Radiance Renewal Serum, i.d. 1150157", GNPD—Global New Products Database, Jul. 1, 2009, p. 1-5.*
International Search Report for corresponding International Application No. PCT/GB2010/051633 dated Aug. 18, 2011.
Collober I. et al, "Activity of Vittel water on proliferation of human fibroblasts, proliferation and differentiation of human keratinocytes", Kluwer Academic Publishers, Dordrecht, NL, vol. 16, No. 4, Jan. 1, 1994 (Jan. 1, 1994), pp. 149-160, XP000953265, Issn: 0142-5463.
"Dimple Vanisher, i.d. 1146830", GNPD—Global New Products Database, Jul. 1, 2009 (Jul. 1, 2009), pp. 1-5, XP55004233.
"Radiance Renewal Serum, i.d.1150157", GNPD—Global New Products Database, Jul. 1, 2009 (Jul. 1, 2009), pp. 1-6. XP55004235.

* cited by examiner

*Primary Examiner* — Jianfeng Song
(74) *Attorney, Agent, or Firm* — Renner, Otto, Boisselle & Sklar, LLP

(57) ABSTRACT

Cosmetic preparations and formulations are described, comprising high concentration (from at least 75% to at least 95%) of thermal mineral waters within the aqueous portion of the formulation. In preferred embodiments, the thermal mineral waters are rendered more bioavailable by pre-fermentation with a microorganism such as the yeast *Saccharomyces cerevisiae*. Formulations are also described in which at least a portion of the thermal mineral water is incorporated into phospholipid liposomes.

14 Claims, No Drawings

COSMETIC PREPARATIONS

This application is a national phase of International Application No. PCT/GB2010/051633 filed Sep. 30, 2010, which claims priority to GB Patent Application No. 0917254.5 filed Oct. 2, 2009.

FIELD OF THE INVENTION

The invention relates to cosmetic preparations and methods for their production.

BACKGROUND

The use of naturally-occurring thermal springs for the improvement of health and well-being of individuals has been known for centuries. In Roman times, thermal spas such as those in Bath in the UK and the Óbuda-Újlak baths in the Acquincum region of Budapest, Hungary, were an important part of cultural, social and healing activities of the time, and remain so to this day.

It has long been known that thermal mineral water can have beneficial effects on many medical conditions, and on the quality of users' skin, but the precise mechanisms are not yet fully understood. Research into these mechanisms is ongoing, but an increasing number of scientific double-blind studies demonstrate that the efficacy is real.

It is also known, in a nutritional context, that minerals are important for the health of skin, and that they are essential co-factors for a large number of enzymes connected with skin regeneration and prevention of oxidative damage.

Minerals are not, of course, synthesised by the human body, and for the most part are taken in as part of the diet. During digestion, the minerals are absorbed in the gut. However, for direct topical application, in order to target the minerals to the skin cells, absorption of minerals through the skin is poor, because, in their ionised state, penetration through the epidermis is limited.

It is an object of the present to provide improved cosmetic formulations that overcome some of these difficulties.

SUMMARY OF THE INVENTION

Accordingly, the invention provides a cosmetic formulation wherein at least 75% of the water content comprises a thermal mineral water. The inventors have found that, surprisingly, formulating a cosmetic product such as a moisturising cream, serum, exfoliant or the like to contain a high concentration of thermal mineral water allows the beneficial effects of the mineral water to be manifested in the skin. In preferred formulations, at least 80%, 85%, 90% or even 95% of the water content comprises such thermal mineral water. The use of such high mineral content cosmetic formulations is referred to as Mineral Cosmetology®.

Preferably, at least part of said thermal mineral water comprises thermal mineral water in which the mineral content has been rendered more bioavailable by the culture of microorganisms within it. It has been shown in oral absorption studies of minerals (Boza, J. J. et al, J. Nutrition, 1995, vol. 125 (6), 1611-1616) that oral absorption of minerals that have been pre-fermented with a microorganism, and especially a yeast such as *Saccharomyces cerevisiae* is significantly enhanced when compared to non-fermented minerals. The inventors have found that the use of such fermented mineral waters also has benefits when used at high concentration in a cosmetic formulation, for topical application. The fermentation process leads to incorporation of the mineral within, or associated with, organic molecules that are more able to penetrate into the skin cells. It is preferred, therefore, that fermentation is carried out with a yeast, and most preferably with *Saccharomyces cerevisiae*. In any use of fermented mineral water, it is preferred that said microorganisms are lysed following their culture. More preferably, cell debris is filtered from the water before use, leaving only the soluble organics with their associated minerals.

As explained by Matz et al (ibid.), mineral waters generally are recognised as having an effect on the skin, and balneotherapy has been used for the treatment of many pathological skin conditions especially psoriasis and atopic dermatitis. Matz et al recognise, however, that "absorption [of minerals] through the skin seems to be limited, but there are no precise data on the subject" (ibid., page 133). The present invention improves this uptake into the skin, and has incorporated the effects into cosmetic formulations, suitable for use on a regular basis, rather than taking a balneotherapeutic approach, requiring visits to spas.

Preparation of such fermented waters may be accomplished by formulating a nutrient medium containing the essential elements required by the organism, such as a carbon and a nitrogen source (preferred sources are urea for the nitrogen, and molasses for the carbon source), but using thermal mineral water as the solvent. Such fermentation facilities are available from Active Concepts LLC, Piscataway, N.J., USA. Following culture, the cells are lysed. Preferably, the cells are allowed to autolyse after growth, by means of the intrinsic yeast enzymes. Addition of acid may also be used to speed up the process. Following lysis, insoluble fractions are removed by filtration.

In especially preferred embodiments, at least part of said thermal mineral water is contained within a liposome. Methods for forming liposomes comprising an aqueous core surrounded by a lipid bilayer are well-known in the art, with phospholipid liposomes being especially preferred. Liposomes are thermodynamically stable, and their size may be controlled by choice of surfactant concentration and type. High shear homogenisation may also be used to adjust their size. It is particularly preferred that liposomes for the present invention have a mean size (measured as an equivalent sphere diameter by e.g. laser diffraction) of below about 0.3 µm. Preferred liposomes fall within the range of about 0.15 to 0.2 µm.

In the most preferred embodiments, the mineral content of at least part of said thermal mineral water has been rendered more bioavailable by the culture of microorganisms within it and is contained within a liposome. The inventors have found that this three-faceted approach to making the mineral content (i.e. at least one of the components of the thermal mineral water) available to the skin cells provides a particularly effective formulation. Firstly, incorporating the thermal mineral water at high concentration within a cosmetic preparation, rather than e.g. ingesting the water, brings the active ingredients of the water directly in contact with the skin. Secondly, by use of a pre-fermentation process to render the minerals more bioavailable, the actives are targeted at the epidermis. Thirdly, by incorporating at least a portion of the fermented thermal mineral water within a liposome, the active ingredients are more able to reach the dermis, thereby further enhancing the effect of the preparation.

Also included within the scope of the invention is a cosmetic formulation substantially as described herein.

The term "Thermal Mineral Water" as used in this specification in its broadest sense refers to waters that emerge from the earth at a higher temperature than ambient temperature, and have a high degree of mineralisation. Typically, such mineral waters emerge with a temperature of greater than 20° C., and have a total mineral content of in excess of about 250 p.p.m. Such waters, being of natural origin, do of course vary in their composition and emergent temperature from source to source. One classification of such waters (described in Matz et al, Dermatologic Therapy, Vol. 16, 2003, 132-140) classifies the water temperature as being "cold" (<20° C.), "hypothermal" (20-30° C.), "thermal" (30-40° C.) or "hyperthermal" (>40° C.).

The mineral content of these waters also varies from source to source, but it is considered that those that have particularly advantageous effects on the skin are usually high in sulfate and bicarbonate. Whilst the mineral content of many such thermal mineral waters has been investigated, it is not yet clearly understood which of the components is responsible for its skin-enhancing properties.

In the present invention, mineral waters that that emerge with a temperature of >20° are preferred. More preferably the emergence temperature is greater than 30° C. and most preferably >40° C.

Furthermore, mineral waters having a total mineral content of >250 p.p.m. are preferred. More preferably, the mineral content is >500 p.p.m., and most preferably >1000 p.p.m. An example of a mineral water particularly suitable for the invention is described below, having a total mineral content of ca. 1300 p.p.m.

Some further mineral waters described in Matz et al (ibid.) include those from La Roche-Posay (France), having a total mineral content of ca. 570 p.p.m; water from Bugok (Korea), with a total mineral content of ca. 360 p.p.m. and water from Ipati (Greece) having a total mineral content of ca. 9600 p.p.m.

In the case of the highly mineralised waters, e.g. those having a total mineral content of above 2000 or even 3000 p.p.m., the stability of emulsions in oil-containing formulations might be compromised. In those cases, the thermal mineral water may be diluted with e.g. demineralised water to bring the mineral content to below the above values, the diluted mineral water being used in the formulations at the concentrations recited above.

DESCRIPTION OF PREFERRED EMBODIMENTS

By way of example, three formulations falling within the scope of the invention are described.

Example 1—Lifting Serum

Table 1 gives a formulation for a lifting serum according to the present invention. The serum preferably contains a proportion of thermal mineral water that has been fermented as described. In this example, the thermal mineral water is cultured with *Saccharomyces cerevisiae* to render the mineral content more biavailable, the yeast cells being lysed and filtered from the water before use. In this formulation, approximately 30% of the product comprises such fermented thermal mineral water in phospholipid liposome form. Additional ingredients may be added, including fragrance, vitamins and antioxidants.

TABLE 1

Example formulation: Lifting Serum

| Ingredient | Proportion (% w/w) | Min (%) | Max (%) |
|---|---|---|---|
| Thermal Mineral Water | QS† | — | — |
| Disodium EDTA | 0.1 | 0.02 | 0.25 |
| Sodium Hyaluronate | 0.5 | 0 | 1.5 |
| Fermented Thermal Water in phospoholipid Liposomes | 30 | 0 | 50 |
| Glycerin + Palmitoyl tripeptide-5 | 3 | 1 | 5 |
| Glycerin + Dextran + Caprooyl Tetrapeptide-3 | 2.5 | 1 | 4 |

†QS: Quantity sufficient to bring total to 100%

Example 2—Day Moisturiser

Table 2 gives a formulation for a day moisturiser according to the present invention. Again, the formulation contains a proportion of thermal mineral water that has been fermented as Example 1 to render the minerals more bioavailable, and formulated with phospholipid liposomes to enhance absorption by the skin. In this formulation some 5% (w/w) of the product is comprised of such fermented, liposome-enhanced thermal mineral water.

The moisturiser comprises a lipid portion, emulsified into the aqueous portion by the use of emulsifiers and emulsion stabilisers. The particular emulsifiers identified in the table are particularly useful for forming such emulsions where the aqueous phase has a high mineral content.

TABLE 2

Example formulation: Day Moisturiser

| Ingredient | Proportion (% w/w) | Min (%) | Max (%) |
|---|---|---|---|
| Thermal Mineral Water | QS† | — | — |
| Glycerin | 3 | 1 | 5 |
| Xanthan Gum | 0.2 | 0.1 | 0.3 |
| Emulsifier (Cetearyl Olivate, Sorbitan Olivate) | 4 | 1 | 5 |
| Emulsion stabiliser (Cetostearyl alcohol) | 2 | 0.5 | 5 |
| Lipids (e.g. Shea butter, Jojoba oil and coconut oil) | 5 | 2 | 10 |
| Lubricant (e.g. Cetearyl Ethylhexanoate) | 2 | 0 | 4 |
| Moisturiser (e.g. squalane) | 3 | 0 | 5 |
| Fermented Thermal Water in phospoholipid Liposomes | 5 | 0 | 10 |
| Fragrance (as required) | — | — | — |

†QS: Quantity sufficient to bring total to 100%

Example 3—Refining Moisturiser

Table 3 details a typical formulation for a refining moisturiser according to the present invention. As well as the recited thermal mineral water content, a part of which is associated with phospholipid liposomes, the moisturiser has hyaluronic acid and polysaccharides.

TABLE 3

Example formulation: Refining Moisturiser

| Ingredient | Proportion (% w/w) | Min (%) | Max (%) |
|---|---|---|---|
| Thermal Mineral Water | QS† | — | — |
| Disodium EDTA | 0.1 | 0.02 | 0.25 |
| Sodium hyaluronate | 0.2 | 0 | 0.7 |

TABLE 3-continued

Example formulation: Refining Moisturiser

| Ingredient | Proportion (% w/w) | Min (%) | Max (%) |
|---|---|---|---|
| Thickener (Carbomer—Carbopol) | 0.7 | 0.2 | 1.5 |
| Preservative (e.g. 90% phenoxyethanol + 10% ethylhexylglycerin) | 1 | 0 | 2 |
| Fermented Thermal Mineral Water | 1 | 0 | 10 |
| Fermented Thermal Water in phospoholipid Liposomes | 10 | 0 | 25 |
| Fragrance (as required) | — | — | — |
| Acidity regulator (e.g. NaOH) | 2.3 | 0 | 3 |
| Polysaccharides (e.g *Ascophyllum nodosum* and *Asparagopsis armata* extract—Aldavine ®) | 3 | 0 | 5 |
| Corundum powder | 1 | 0 | 2 |

†QS: Quantity sufficient to bring total to 100%

Thermal Mineral Waters

Thermal mineral waters meeting the specifications outlined herein may be used in the products. A particularly preferred thermal mineral water is, however, that obtained from the Gellert Spa in Hungary. Tables 4 and 5 give typical ionic analyses of cations and anions respectively from this source.

TABLE 4

Cation Analysis

| Cation | mg/l |
|---|---|
| Potassium | 15.8 |
| Sodium | 120 |
| Ammonium | 0.23 |
| Calcium | 160 |
| Magnesium | 52 |
| Iron | 0.03 |
| Manganese | 0.02 |
| Lithium | 0.37 |

TABLE 5

Anion Analysis

| Anion | mg/l |
|---|---|
| Nitrate | 0.4 |
| Nitrite | 0.0 |
| Chloride | 136 |
| Bromide | 0.39 |
| Iodide | 0.03 |
| Fluoride | 2.21 |
| Sulfate | 341 |
| Hydrogen carbonate | 543 |
| Phosphate | 0.00 |

The invention claimed is:

1. A cosmetic formulation wherein at least 75% of the water content comprises a thermal mineral water, at least part of said thermal mineral water comprising thermal mineral water in which the mineral content has been rendered more bioavailable by the culturing within it of microorganisms said microorganism comprising a yeast, wherein at least part of said thermal mineral water is contained within a liposome.

2. The cosmetic formulation according to claim 1 wherein said yeast comprises *Saccharomyces cerevisiae*.

3. The cosmetic formulation according to claim 2 wherein said microorganisms are lysed following their culture.

4. The cosmetic formulation according to claim 3 in which cell debris from lysing has been removed from the water prior to use.

5. The cosmetic formulation according to claim 1 wherein the mineral content of at least part of said thermal mineral water has been rendered more bioavailable by the culture of microorganisms within it and is contained within a liposome.

6. The cosmetic formulation wherein at least 75% of the water content comprises a thermal mineral water, at least part of said thermal mineral water comprising thermal mineral water in which the mineral content has been rendered more bioavailable by the culturing within it of microorganisms said microorganism comprising a yeast, the yeast comprising *Saccharomyces cerevisiae* and wherein at least part of said thermal mineral water is contained within a liposome.

7. The cosmetic formulation according to claim 6 wherein the mineral content of at least part of said thermal mineral water has been rendered more bioavailable by the culture of microorganisms within it and is contained within a liposome.

8. A cosmetic formulation wherein at least 75% of the water content comprises a thermal mineral water, at least part of said thermal mineral water comprising thermal mineral water in which the mineral content has been rendered more bioavailable by the culturing within it of microorganisms, said microorganism comprising a yeast and at least part of said thermal mineral water has been rendered more bioavailable by the culture of microorganisms within it and is contained within a liposome.

9. The cosmetic formulation according to claim 1 wherein the liposome is one of a plurality of liposomes, and a mean size of the plurality of liposomes is 0.15 µm to 0.2 µm.

10. The cosmetic formulation according to claim 6 wherein the liposome is one of a plurality of liposomes, and a mean size of the plurality of liposomes is 0.15 µm to 0.2 µm.

11. The cosmetic formulation according to claim 8 wherein the liposome is one of a plurality of liposomes, and a mean size of the plurality of liposomes is 0.15 µm to 0.2 µm.

12. The cosmetic formulation according to claim 1 wherein the liposome is one of a plurality of liposomes, and the cosmetic formulation comprises 5 wt % to 30 wt % of said thermal mineral water contained within the plurality of liposomes.

13. The cosmetic formulation according to claim 6 wherein the liposome is one of a plurality of liposomes, and the cosmetic formulation comprises 5 wt % to 30 wt % of said thermal mineral water contained within the plurality of liposomes.

14. The cosmetic formulation according to claim 8 wherein the liposome is one of a plurality of liposomes, and the cosmetic formulation comprises 5 wt % to 30 wt % of said thermal mineral water contained within the plurality of liposomes.

* * * * *